(12) United States Patent
Lelièvre et al.

(10) Patent No.: US 10,940,475 B2
(45) Date of Patent: Mar. 9, 2021

(54) GRADIENT-ON-A-CHIP

(71) Applicant: Purdue Research Foundation, West Lafayette, IN (US)

(72) Inventors: Sophie Andree Lelièvre, West Lafayette, IN (US); Babak Ziaie, West Lafayette, IN (US); Manuel P. Ochoa, Lafayette, IN (US); Rahim Rahimi, West Lafayette, IN (US); Farzaneh Atrian, Lafayette, IN (US); Shirisha Chittiboyina, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 184 days.

(21) Appl. No.: 15/939,744

(22) Filed: Mar. 29, 2018

(65) Prior Publication Data

US 2018/0280976 A1 Oct. 4, 2018

Related U.S. Application Data

(60) Provisional application No. 62/478,674, filed on Mar. 30, 2017.

(51) Int. Cl.
*B01L 3/00* (2006.01)
*B01F 5/06* (2006.01)
(Continued)

(52) U.S. Cl.
CPC ...... *B01L 3/502753* (2013.01); *B01F 5/0644* (2013.01); *B01F 5/0647* (2013.01); *B01F 13/0059* (2013.01); *B01F 15/0404* (2013.01); *B01L 3/50273* (2013.01); *B01L 3/502707* (2013.01); *B01L 3/502715* (2013.01); *B01L 3/502746* (2013.01); *B01L 3/502761* (2013.01); *B01L 3/502776* (2013.01); *C12M 23/16* (2013.01); *C12M 23/20* (2013.01); *C12M 23/22* (2013.01); *C12M 35/08* (2013.01); *C12M 41/00* (2013.01); *C12M 41/46* (2013.01); *G01N 33/5038* (2013.01); *G01N 33/525* (2013.01); *B01L 2200/0647* (2013.01);
(Continued)

(58) Field of Classification Search
CPC ........ B01L 3/502753; B01L 3/502707; B01L 3/502715; B01L 3/50273; B01L 3/502746; B01L 3/502761; B01L 3/502776; B01L 2200/0647; B01L 2200/0694; B01L 2300/0867; B01L 2300/0877; B01L 2300/123; B01L 2300/126; B01L 2400/0406; G01N 33/5038; G01N 33/525; B01F 5/0644; B01F 5/0647; B01F 13/0059; B01F 15/0404; C12M 23/16; C12M 23/20; C12M 23/22; C12M 35/08; C12M 41/00; C12M 41/46
USPC ................................ 422/551, 552, 553, 554
See application file for complete search history.

(56) References Cited

U.S. PATENT DOCUMENTS 2,561,339 A * 7/1951 Chediak ................ B01L 3/5085
422/552
4,828,386 A * 5/1989 Matkovich ............. G01N 21/03
356/246

(Continued)

*Primary Examiner* — Brian J. Sines
(74) *Attorney, Agent, or Firm* — Purdue Research Foundation; Zhigang Rao

(57) ABSTRACT

Disclosed herein is a cell culture device and its applications of creating gradient of chemicals or gradient of cells to mimic the in vivo physiological conditions of homeostasis.

9 Claims, 13 Drawing Sheets

(51) Int. Cl.
  *C12M 3/06* (2006.01)
  *G01N 33/50* (2006.01)
  *G01N 33/52* (2006.01)
  *C12M 1/00* (2006.01)
  *C12M 1/34* (2006.01)
  *B01F 15/04* (2006.01)
  *C12M 1/42* (2006.01)
  *B01F 13/00* (2006.01)

(52) U.S. Cl.
  CPC .............. *B01L 2200/0694* (2013.01); *B01L 2300/0867* (2013.01); *B01L 2300/0887* (2013.01); *B01L 2300/123* (2013.01); *B01L 2300/126* (2013.01); *B01L 2400/0406* (2013.01); *B01L 2400/0622* (2013.01)

(56) References Cited

U.S. PATENT DOCUMENTS

| | | | | |
|---|---|---|---|---|
| 5,200,152 | A * | 4/1993 | Brown | B01L 3/5027 356/244 |
| 5,540,891 | A * | 7/1996 | Portmann | B01L 3/5085 206/443 |
| 6,051,191 | A * | 4/2000 | Ireland | B01L 3/5085 356/246 |
| 2005/0169962 | A1* | 8/2005 | Bhatia | G01N 33/5044 424/423 |
| 2010/0247386 | A1* | 9/2010 | Deutsch | C12M 23/22 422/553 |
| 2011/0003717 | A1* | 1/2011 | Smith | B01L 3/5085 506/33 |
| 2015/0018226 | A1* | 1/2015 | Hansen | G01N 33/569 506/9 |
| 2015/0177226 | A1* | 6/2015 | Lelievre | C12M 23/12 435/305.1 |

* cited by examiner

GRADIENT-ON-A-CHIP

CROSS REFERENCES

This application claims the benefit of U.S. Provisional Application 62/478,674, filed on Mar. 30, 2017. The entire disclosure therein is expressly incorporated for reference.

FIELD OF INVENTION

This disclosure relates to a novel device for creating an open cell culture system with controlled gradient of analytes and chemicals of interest. Particularly, the device creates a gradient-on-a-chip in which analytes or chemicals may be progressively mixed with the cell culture medium within connected microchannels and diffused upward into the open cell culture window.

BACKGROUND

Biomolecule gradients have been shown to play roles in a wide range of biological processes including development, inflammation, wound healing, and cancer metastasis. Elucidation of these phenomena requires the ability to expose cells to biomolecule gradients that are quantifiable, controllable, and mimic those that are present in vivo.

Biomolecular gradients are an important, evolutionarily-conserved signaling mechanism for guiding the growth, migration, and differentiation of cells within the dynamic, three-dimensional environment of living tissue. Gradients play essential roles in many phenomena including development, inflammation, wound healing, and cancer. Interest in elucidating these phenomena has led to the development of numerous in vitro methods for exposing cells to chemical gradients. In combination with in vivo studies, these methods have revealed gradient signaling to be an intricate, highly-regulated process, in which the ultimate cellular response is determined by the unique complement, concentration, and spatiotemporal characteristics of the gradients to which cells are exposed.

Traditional in vitro gradient-generating methods have been instrumental in shaping our current understanding of gradient signaling, but they are not ideal for examining the quantitative or combinatorial nature of gradient signaling due to their inability to produce precise, user-defined gradients with tailored spatial and temporal profiles. The chemical gradients generated by traditional methods often evolve unpredictably or uncontrollably over space and time, and can be difficult to characterize quantitatively. The gradients form and dissipate within a few hours, greatly limiting the cell types and questions that can be studied. Elucidation of the complexities of gradient signaling requires more detailed knowledge and control over the spatiotemporal distribution of chemical species in the extracellular environment and the ability to directly visualize cells within that environment.

Another important outcome of having gradients of molecules in the tissue microenvironment is to create heterogeneous alterations within that tissue. Therefore, drugs used to treat a specific condition might be more or less successful depending on the degree of alteration of a tissue induced by a chemical. Using a cell culture system that recapitulates different degrees in disease progression would enable scientists to know below (or above) which level of degradation or alteration the drug is acting. Similarly, a particular condition of the matrix might influence the impact that a concentration of a chemical has on the tissue and consequently, raise or lower the level at which a drug would stop or start working.

The importance of biomolecular gradients in directing the growth, differentiation, and migration of various cell types in vivo has motivated researchers to develop numerous methods for generating chemical gradients in vitro.

Biological hydrogels made from collagen, fibrin, or agarose are commonly used to establish biomolecule gradients around cells in vitro. Unfortunately, the biological hydrogel method offers little control over the spatiotemporal evolution of the gradient and generates gradients with poor reproducibility. The use of cell-based biomolecule sources (i.e. explants, transfected cell lines) results in gradients that are highly variable and difficult to quantitatively characterize due to the unknown level of biomolecule secreted by the cells.

Other traditional in vitro gradients include micropipette generated gradients, various chambers, and recently developed microfluidic method. But, they all suffer the similar shortcomings as biological matrix gels. The ability to create complex, user-defined gradient environments is desired to enable quantitative elucidation of multi-gradient signal integration, and provide the specific recipes for engineering the proliferation, migration, and differentiation of a variety of cell types. They are also necessary to identify the impact of drugs on cells affected by a certain level of analyte or chemical using a continuous system in which the exact response threshold may be determined.

SUMMARY OF THE INVENTION

This disclosure provides an open cell culture device for creating a "gradient-on-a-chip". The device comprises from bottom to top:
  an optically transparent and machinable bottom fixture;
  a moldable/castable silicone/rubber material based microfluidic spacer with laser defined microchannels;
  a paper bifurcating mixer, wherein the dimensions of the paper bifurcating mixer are configured to fit into the microchannels of the microfluidic spacer;
  an optically transparent polymer film based membrane with laser defined micro-apertures, wherein the micro-apertures are positioned downstream to the microchannels; and
  an optically transparent and machinable cover fixture with an exposure aperture as cell culture chamber, and at least two inlets and one outlet for tubing.

In some embodiment, the optically transparent and machinable cover/bottom fixtures are acrylic plates.

In some embodiment, the optically transparent polymer based membrane is a polyethylene terephthalate (PET) membrane.

In some embodiment, the moldable/castable silicone/rubber textured microfluidic spacer is made of polydimethylsiloxane (PDMS).

In some embodiment the aforementioned open cell culture device further comprises a smooth hydrophilic cellulose-based film as the substrate, wherein the substrate is coated with or without extracellular matrix for cell culture. The substrate is laid within the area of micro-apertures of the polymer film based membrane and it may be cellulose acetate.

In some embodiment the aforementioned microchannels are about 200 μm deep.

In some embodiment the aforementioned micro-apertures are evenly distributed over an area of the exposure aperture's size, and are configured to have adequate access to an underlying chemical gradient and to maintain the stiffness to keep the paper mixer inside the microchannels.

In some embodiment the aforementioned open cell culture device acrylic bottom and cover fixtures are each about 5 mm thick.

In some embodiment the aforementioned paper bifurcating mixer is porous hygroscopic material providing capillary forces for continuous, leak-less flow.

This disclosure further provides a method to create an analyte or chemical gradient to culture cells in an open cell culture device, comprising:

Assembling the aforementioned open cell culture device;
Seeding a layer of cells on a smooth hydrophilic cellulose-based film substrate with or without additional extracellular matrix in the exposure aperture;
Providing controlled length of tubing filled with cell culture medium and at least one analyte or chemical flowing to the at least two inlets;
Allowing the cell culture medium and the analyte to be diffused from underneath the layer of cells;
Providing controlled length of tubing to the outlet with appropriate force taking out the cell culture medium;
Controlling the flow rate of the inlet tubing and outlet tubing until the equilibrium of the cell culture medium flow between the inlets and the outlet is reached; and
Optionally removing different zones of the cell culture on the paper substrate from the exposure aperture; and
Analyzing the cell culture on the paper substrate to establish the analyte or chemical gradient effect on the cells.

In some embodiment the aforementioned smooth hydrophilic cellulose-based film is cellulose acetate.

In some embodiment the aforementioned analyte is $H_2O_2$ generated Reactive Oxygen Species (ROS), a chemical compound, a type of cell or a cellular factor.

In some embodiment the aforementioned layer of cells on the smooth hydrophilic cellulose-based film is in 2-D culture for days before loading to the exposure aperture.

In some embodiment the aforementioned layer of cells on the smooth hydrophilic cellulose-based film is in 3-D culture for days before loading to the exposure aperture.

In some embodiment the aforementioned cells are selected from the group consisting of non-neoplastic cells, preinvasive cancer cells and invasive cancer cells.

In some embodiment the aforementioned analyte is $H_2O_2$ and the gradient effect is analyzed by optical approach or catalyst approach.

In some embodiment the aforementioned analyte/chemical is a compound or a cellular factor, and the gradient effect is analyzed by studying the nucleus morphology change or other cellular components variation among different zones of the cell culture in the exposure aperture.

In some embodiment the aforementioned first inlet comprising a given concentration of $H_2O_2$ in cell culture medium, and the second inlet comprising cell culture medium.

In some embodiment the aforementioned paper substrate creates an air-liquid interface, depending on the tissue in culture.

In some embodiment the aforementioned paper bifurcating mixer is disposable.

In some embodiment the aforementioned cell culture can be analyzed by microscopy.

In some embodiment the aforementioned cell culture on the substrate paper is removed and immunostained to observe cellular and extracellular organization and function.

In some embodiment the aforementioned cell culture on the substrate is removed and cut into pieces to prepare cellular extracts corresponding to different zones (e.g., low, middle, high concentration ranges) in the gradient.

In some embodiment the aforementioned flow rates are controlled by pumps.

These and other features, aspects and advantages of the present invention will become better understood with reference to the following figures, associated descriptions and claims.

DETAILED DESCRIPTION

Figures 1, 1A, 1B, 1C, 1D, 1E, 1F:
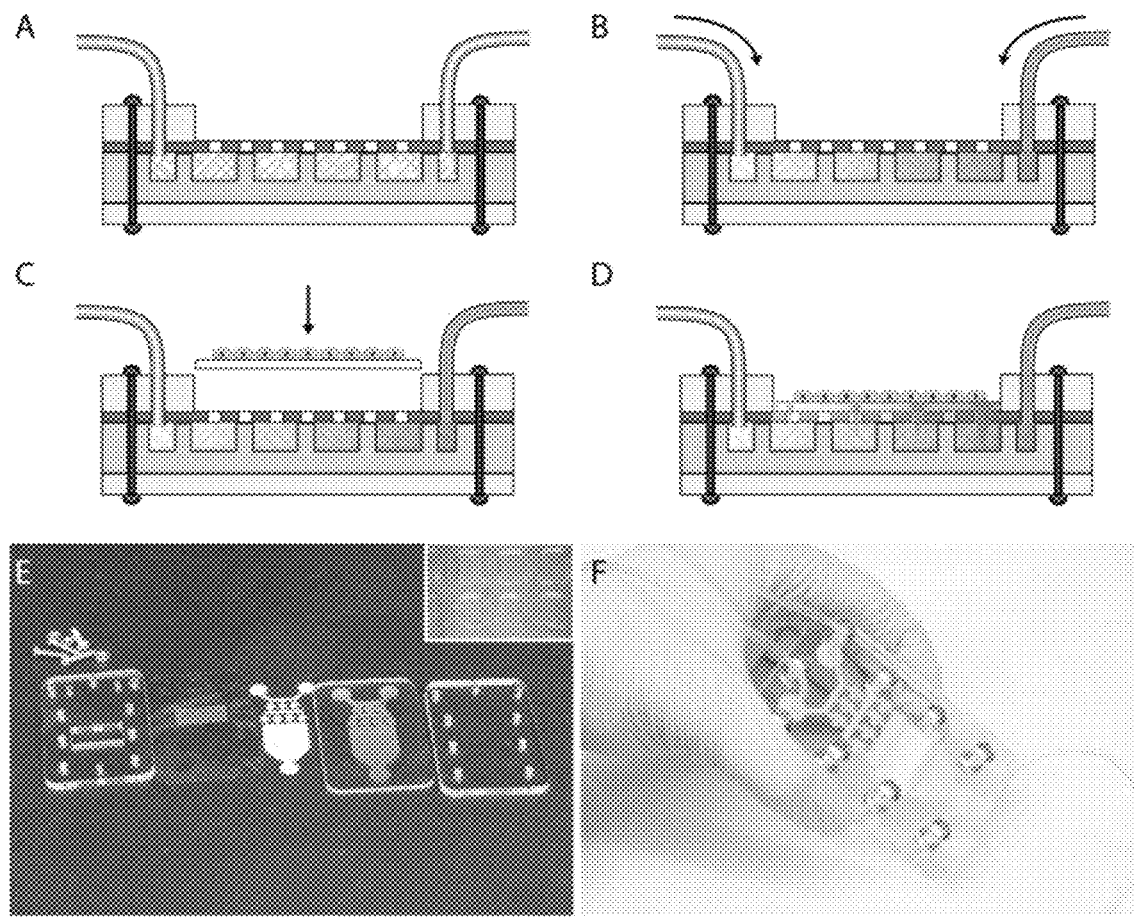
FIG. 1. The design of the microfluidic device enables cell exposure to a chemical gradient via an open culture chamber.
(FIG. 1A) Illustration of assembled open access microfluidic concentration gradient generator secured in place with acrylic fixtures (black rods), (FIG. 1B) fluidic inlets (arrows) with constant flow rate to create a stable concentration gradient within the cell culture aperture, (FIG. 1C) placement of cell culture samples in the open culture chamber, (FIG. 1D) diffusion of the concentration gradient (purple arrows) across the laser-machined PET membrane, (FIG. 1E) photograph of the microfluidic components, including (from left to right) top acrylic fixture with cell culture aperture, PET membrane, paper microfluidic insert, PDMS microfluidics, and bottom acrylic fixture; the inset is a high magnification of laser-machined micro-apertures on the PET membrane.
(FIG. 1F) Final assembled device FIG. 2. Gradient formation occurs in the microchannels.

While the concepts of the present disclosure are illustrated and described in detail in the figures and the description herein, results in the figures and their description are to be considered as exemplary and not restrictive in character. It is understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Oxidative stress-mediated cancer progression depends on exposure to reactive oxygen species (ROS) in the extracellular matrix (ECM). To study the impact of ROS levels on preinvasive breast cancer cells as a function of ECM characteristics, we created a gradient-on-a-chip in which $H_2O_2$ progressively mixes with the cell culture medium within connected microchannels and diffuses upward into the open cell culture window. The device utilizes a paper-based microfluidic bifurcating mixer insert to prevent leakage and favor an even fluid distribution. The gradient was confirmed by measuring $H_2O_2$ catalyzed into oxygen, and increasing oxidative DNA damage and protective (AOP2) response were recorded in 2D and ECM-based 3D cell cultures. Interestingly, the impact of ROS on nuclear shape and size (annunciating phenotypical changes) was governed by the stiffness of the collagen I matrix, suggesting the existence of thresholds for the phenotypic response to microenvironmental chemical exposure depending on ECM conditions.

As used herein, an "acrylic top fixture with a cell culture aperture" is an acrylic plate with a laser cut opening for cell culture. It is noted that the acrylic plates can be substituted by any other material that is optically transparent (and machinable, e.g., by laser). The opening is also referred as "exposure aperture" or cell culture chamber throughout the application, and it covers the collective size of the underlying PET membrane micro-apertures.

As used herein, "paper substrate" (sometimes referring to the cellulose acetate), can be substituted by any smooth hydrophilic paper-like film or a smooth hydrophilic cellulose-based film.

As used herein, a "paper based mixer" is a filter paper that is cut into the same shape as the microfluidic portion of polydimethylsiloxane (PDMS) layer, and fits into the microchannels of PDMS layer. The paper-based mixer is also referred to as paper insert, paper bifurcating mixture throughout the application. In some embodiment, the paper based mixer is the same or similar material as the paper substrate, i.e., both of them are hydrophilic cellulose-based film.

As used herein, the microfluidic portion of polydimethylsiloxane (PDMS) layer can be substituted by any moldable/castable silicone/rubber material.

As used herein, the polyethylene terephthalate (PET) membrane can be substituted by any optically transparent polymer based membrane.

As used herein, "microchannels" are part of the microfluidic concentration gradient generator. They are generated by laser ablation in PDMS layer and fit paper based mixer therein. Microchannels may be patterned, bifurcated or any other designs that fit the purpose of generating a microfluidic concentration gradient with the control of inlet and outlet flow rate.

As used herein, "micro-apertures" are small squares that are evenly distributed on the PET membrane corresponding to the size of "exposure aperture" and positioned downstream of the microchannels from the underlying paper based mixer and PDMS layer.

The long-time proposal that the tissue microenvironment plays a role in cancer has led scientists to rethink cell culture approaches. Studies with cancer cells in vitro used to be conducted in majority under two dimensional (2D) conditions, on flat and rigid substrates. Yet, recognizing the importance of signaling by the extracellular matrix (ECM) in vivo has helped design three-dimensional (3D) cell culture systems with which tremendous differences in cell phenotypes, when comparing with 2D cultures, have been increasingly reported. In light of the demonstrated influence of the ECM on cell differentiation, nuclear organization and gene expression, and of the alterations in gene expression and chromatin organization that accompany cancer development, it has become clear that the type of ECM used in 3D cell culture matters.

The production of chemicals such as reactive oxygen species (ROS) is frequent in the microenvironment and may lead to oxidative stress, a cellular condition implicated in several pathologies, including cancer.

Extracellular ROS are cleared by antioxidant proteins, such as catalase or superoxide dismutase that are expressed at low levels in the tumor microenvironment[10], leading to high levels of oxidative stress in most cancers including that of the breast[11]. Due to enzymatic activity of NADPH oxidases such as NOX1, superoxide anions ($O_2^-$) that are less reactive are converted to $H_2O_2$, a highly reactive subgroup of ROS. Oxidative stress is illustrated by DNA damage inside cells, but when ROS are present in the stroma, they also influence the stiffness of the ECM following the activation of stromal fibroblasts. Stiffness is usually increased by the presence of ROS[9], a change that has also been associated with cancer progression[13]. However, the impact of increased stiffness per se on the response of cancer cells to ROS is not known, as it is linked to fibroblast activation that also leads to the release of paracrine factors that may influence cancer cells.

A cell culture system that can provide a controlled ROS or other chemical gradient in the ECM is need to mimic the in vivo cell environment.

In this disclosure, we create a chemical gradient model in a small cell culture system with which significantly different cellular responses are measured. The chemical can be anything from oxygen gas, or cellular factors and chemical compounds that may have an impact on the cells in the system. Non-neoplastic cells, pre-invasive cells or invasive cancer cells can be first cultured in a paper substrate for a suitable time period, then transferred to the exposure aperture in the device to experience the gradient caused effect. Analyzing the gradient effect can be optically, catalytically or through dissecting the cell components via biochemical means, such as western blot, fluorescent imaging, etc.

Previous microfluidics-based studies produced oxygen gradients, but analyses were limited by the size of the cell culture chamber and the difficulty in harvesting the cells. Our open-access microfluidic gradient system is easy to assemble, and it is convenient to gather cell cultures for additional processing, notably to cut the cultures into regions corresponding to different ROS concentration ranges for quantitative protein analysis. Images of cell culture in the open access microfluidic gradient system can be recorded with a standard fluorescence microscope. Other means of studying the chemical gradient impact on the cell culture with or without additional extracellular matrix, including, but not limited to collecting cell culture to analyze the protein expressions, nucleus morphology, drug responses, etc., are within the realm of the instant disclosure.

An important characteristic of the device is the presence of the paper inserts within the microchannels, enabling even fluid spread and reproducibility of the system, as shown by the relatively small error bars when comparing three biological replicates for the different readouts used in this study.

The microfluidics design is performant in creating a gradient as shown in the examples, not only by the measurements of ROS, but also by the incremental cell responses for all the markers studied. As an exemplary embodiment, hydrogen peroxide was chosen because it is a relatively more stable form of ROS that has been widely used in cell based assays to induce oxidative stress[39]. The parameters of ROS-induced injury as well as those of oxidative stress response showed increasing levels with increasing ranges of ROS concentrations.

Materials and Methods
Materials Used for the Microfluidic System Design:

The microfluidic device was fabricated by laser micromachining of common laboratory materials including acrylic, polyethylene terephthalate (PET), and filter paper (Whatman®, cellulose grade 1, 180 μm thick) using a commercial laser engraver system (Universal Laser Systems, Inc., Scottsdale, Ariz.). Specifically, the bottom microfluidic portion was laser ablated to create 200 μm deep microchannels into a polydimethylsiloxane (PDMS) layer (thickness ~1.5 mm, prepared in a 10:1 ratio and cured at 80° C. for 3 h). The filter paper was laser cut into a microfluidic mixer with dimensions such that it fitted into the laser ablated channels of the PDMS layer. Next, the PDMS microfluidic platform with the paper insert was covered with a PET sheet that included laser defined micro-apertures downstream of the microchannels. The micro-apertures were 400 μm×400 μm squares with 400 μm spacing over 2.2×1.1 cm$^2$. The size and distribution of the apertures were chosen such that adequate access to the underlying chemical gradient was provided to the cell culture surface opening while simultaneously bringing the necessary stiffness to keep the paper-based mixer inside the PDMS channels. The assembled components were mounted between two acrylic layers (thickness ~5 mm) and secured with nine screws. The inlets and outlet of fluid and 2.2×1.1 cm$^2$ opening for cell culture were created by laser cutting the top acrylic cover. The cell culture opening on the top acrylic cover was in alignment with laser machined micro-apertures and the underlying microfluidic concentration gradient generator. Once assembled the device included from bottom to top, an acrylic stand, a PDMS microfluidic spacer, a paper bifurcating mixer, a micro-aperture membrane made of PET film and an acrylic cover.

Measurement of Reactive Oxygen Species (ROS) gradient

The performance of the open-access gradient generator was validated using several approaches. In the optical approach the concentration gradient was evaluated by introducing red-dyed (Assorted food dye, Walmart) water and undyed deionized water at the same flow rate of Q1 (100 μl min$^{-1}$) into the two inlets of the platform. The solution was withdrawn from the outlet at a rate equal to twice the inlet Q3=2×Q1 (200 μl min$^{-1}$) to accommodate for liquid flow from two inlets. The open chamber was divided into 10 sections and relative red color in each section was measured using image processing software (Photoshop CS6). The color intensity (relative to the lowest measured) was plotted as a function of distance along the chamber width. For the catalyst approach, the red dye was replaced with 0.5% $H_2O_2$ solution prepared by mixing 30% $H_2O_2$ with deionized (DI) water (ratio 1:60). The DI water was introduced at a flow rate Q1=100 μl min$^{-1}$ through one inlet, and the 0.5% $H_2O_2$ solution was introduced at the same flow rate Q2=Q1=100 μl min$^{-1}$ through the other inlet of the platform to produce the $H_2O_2$ based ROS gradient. The withdrawal flow rate was twice the inlet (200 μl min$^{-1}$). The ROS gradient was indirectly measured by converting the $H_2O_2$ into oxygen and subsequently measuring the oxygen generation rate with a commercial fiber-optic oxygen sensing probe (NeoFox, OceanOptics, Dunedin, Fla.). Conversion of $H_2O_2$ to oxygen was achieved via a catalyzing reaction. Briefly, nanoparticles of $MnO_2$ (catalyst) were mixed with agarose before gel formation. Then, the 2 mm thick agar gel was placed on the cellulose acetate cell culture membrane. The $H_2O_2$ that diffused into the agarose gel was catalyzed into oxygen; the resulting level of dissolved oxygen provided indirect information about the local level of ROS species. The gradient was also visualized via chemiluminescence achieved by evenly spraying two solutions onto the bed fluid containing the ROS gradient. The first solution was made by dissolving 0.1 g of potassium ferricyanide in 10 ml of DI water. This solution served as a catalyzing agent. The second solution was prepared by dissolving 0.1 g of luminol and 0.8 g of potassium hydroxide in 15 ml of DI water.

Cell Culture

Human mammary epithelial non-neoplastic S1 cells[17] [used between passages 52 to 60], preinvasive S2 cells[18] [used between passages 218+2 and 218+10] and invasive T4-2 cells[19] [used between passages 28+4 and 28+10] that belong to the HMT-3522 breast cancer progression series, were cultured in H-14 medium, i.e., Dulbecco modified Eagle medium (DMEM) (Invitrogen Inc., Carlsbad, Calif.) supplemented with additives, prolactin (30.3 IU/ml; Sigma-Aldrich, St Louis, Mo.), insulin (100 μg/ml; Sigma-Aldrich), hydrocortisone (0.5 mg/ml; BD Biosciences, San Jose, Calif.), beta-estradiol (2.67×10$^{-5}$ μg/ml; Sigma-Aldrich), selenium (2.6 μg/ml; BD Biosciences) and transferrin (20 mg/ml; Sigma-Aldrich)[20]. The culture medium also included epithelial growth factor (EGF) (20 mg/ml; BD Biosciences) until day 6 of culture, after which EGF was omitted from the culture medium to ensure proliferation arrest in 3D culture. Cell culture was performed at 37° C. in a humidified environment with 5% carbon dioxide and the culture medium was changed every three days for the S1 cells and every two days for S2 and T4-2 cells. Seeding densities in 2D culture were 22600 cells/cm$^2$ for S1 cells and 11900 cells/cm$^2$ for S2 and T4-2 cells. In 3D culture seeding densities were 86300 cells/cm$^2$ for S1 cells in the presence of Engelbreth-Holm-S warm (EHS) mouse derived Matrigel (Corning Life Sciences, Tewksbury, Ma.) or within collagen-1 rich Collymer matrix (GeniPhys™, Zionsville, Ind.) and 43150 cells/cm$^2$ for S2 and T4-2 cells. Culture in Matrigel was done according to previously described methods[20]. Briefly, 42 μl of Matrigel per cm$^2$ was used for the drip method with cells in 150 μl of medium, dripped on the gel-coated surface, before adding another 150 μl of medium with 10% EHS gel drop-by-drop all over the culture surface five minutes later (in the end seeding involved 3.47×10$^4$ S1 cells cells/cm$^2$ per 55 μl of Matrigel; 1.74×10$^4$ S2 or T4-2 cells/cm$^2$ per 55 μl of Matrigel). Collymers were prepared at different degrees of stiffness based on the formula provided by the manufacturer. S1 cells were cultured in 800 Pa Collymers stiffness, S2 cells were cultured in 800 Pa and 1500 Pa Collymers stiffness and T4-2 cells were cultured in 1500 Collymers stiffness. For the S2 cells, since they are preinvasive and nodules are surrounded by a basement membrane, basement membrane formation inducer laminin 111 (Corning) was mixed at 76 μg/ml final concentration with Collymers. For the Collymers thin-embedded culture, the surface was coated with 14 μl/cm$^2$ of Collymers of the desired stiffness. Collymers become opaque when they form a gel by incubation five minutes at 37° C. Cells were mixed with Collymers at the following concentrations per surface of culture and Collymers volume units: 4500 cells/cm$^2$/μl for S1 cells and 2262 cells/cm$^2$/μl for S2 and T4-2 cells. Following centrifugation at 2950 g for five minutes, the cells needed for each culture surface were put in solution in 5 μl of H-14 medium. Then, the cell suspension was mixed with Collymers (55 μl/cm$^2$ of culture surface) by gentle pipetting before coating on the cell culture surface, drop-by-drop all over the surface, and spreading with the pipette tip to ensure even distribution over the culture surface. After incubation five minutes at 37° C., 500 μl medium was added on top of the Collymers-embedded cells.

Cellulose acetate-based paper was sterilized under Ultra-Violet (UV) in the cell culture hood for 24 hours prior to cell culture. For tests that did not make use of the gradient-on-a-chip device, paper strips were cut to fit the wells of a 4-well plate (Thermofisher Inc., Waltham, Mass.) for 2D cell culture or to fit the wells of a four-well chambered slide (Thermofisher Inc.) for 3D cell culture. For work with the gradient-on-a-chip, paper was cut to fit the 2.1×1.1 cm$^2$ chamber size, and when coated with gel, they were gently pressed with a glass coverslip (VWR, International, Radnor, Pa.) to ensure even distribution of the gel on the paper substrate. The coverslip was removed gently once the matrix (Collymer or Matrigel) had become a solid gel. Cells were used at day 6 of 2D culture or, to allow time for differentiation, at day 8 of 3D culture.

Fluorescence Immunostaining

Antibodies used included Anti-rabbit Caspase-3 (Cell Signaling Technologies, Boston, Mass. 1/400 dilution), AOP2 (Abcam, Cambridge, Mass.; 2 μg/ml) and γ-H2AX (Ser139; Millipore, clone JBW301, 3.3 μg/ml). Cells were fixed with 4% paraformaldehyde (Sigma-Aldrich) and processed for immunostaining as described previously[21]. Nuclei were counter-stained with DAPI (50 μg/ml; this concentration is higher than usual in order to get a clearer signal in the presence of the paper substrate). The paper with cells was placed, facing down, on a drop of antifade on a glass slide and dried overnight. Images were recorded using Q-capture image acquisition software linked to a B1500X inverted fluorescence microscope (Olympus, Waltham, Mass.), with 10× objective (NA=0.25).

Production of the ROS Gradient

A NE-4000X dual syringe pump (New era pump systems Inc., Farmingdale, N.Y.) was exposed to UV overnight before the day of experiments. The flow rate was adjusted to 0.1 ml/h, and using a 60 ml syringe a continuous inflow of medium and $H_2O_2$ (250 μM) through the inlets was maintained. The second pump was connected to the outlet to remove the medium at 0.2 ml/h to avoid overflow of liquids in the cell culture aperture of the device. The flow rate for the outlet pump was twice that of the incoming flow rate to accommodate for the use of two inlets. The paper strip with cells in 2D or 3D culture was placed in the cell culture slot of the device and exposed to the ROS gradient for four hours.

Preparation of Total Cell Extracts and Western Blot Analysis

Papers with 2D or 3D cell cultures were cut into three pieces of equal length (7 mm) that represented exposure to three different concentration ranges of $H_2O_2$, i.e., low, medium and high. Cells from 2D culture were scraped off the surface and centrifuged at 800 g for 15 minutes in PBS buffer mixed with protease inhibitors, pefabloc (1 mg/ml; Sigma-Aldrich), NaF (250 μM; Sigma-Aldrich), aprotinin (1 m/ml; Sigma-Aldrich). Cells from 3D culture with Matrigel were released from the gel by using 100 μl/cm$^2$ dispase (BD Biosciences) upon incubation for 30 min at 37° C. Protein samples were prepared as previously described[22], and protein concentrations were measured using a Bio-Rad Protein Assay kit (Bio-Rad laboratories, Hercules, Calif.). The samples (30 m proteins) were incubated with 6× loading buffer (0.375 M Tris at pH 6.8, 12% sodium dodecyl sulfate (SDS), 60% glycerol, 0.6 M dithiothreitol (DTT), 0.06% bromophenol blue) at 37° C. for 20 minutes, loaded into the wells of a 10% SDS polyacrylamide gel and run by electrophoresis at 55 mA current on a Bio-Rad gel apparatus (Bio-rad laboratories). Proteins were transferred onto a nitrocellulose membrane (Bio-rad laboratories) at 220 mA for 2.5 hours maximum. The membrane was blocked in 5% milk prepared in TBST (pH 8.0 Tris buffer with 0.5% Tween 20) overnight at 4° C. and incubated with the primary antibody (mouse anti-8-OHdG (Abcam, 4 μg/ml) overnight at 4° C. After three washes with TBST buffer, the membrane was incubated with antimouse horse-radish peroxidase conjugated secondary antibody (GE Healthcare, Pittsburgh, Pa.; 1:10000 dilution) in blocking buffer for 40 minutes at room temperature. Immunoreactive protein bands were detected using ECL WesternSuper plus (Thermofisher). Images of the protein bands were analyzed using GeneSys Image Acquisition Software version 3.9.1 (Syngene, Frederick, Md.) and normalized to lamin B. All densitometric analyses were performed with Image J (https://imagej.nih.gov/ij).

Nuclear Morphology Assessment

Nuclear circularity and nuclear area were measured using the ImageJ software by outlining the nuclear shape based on DAPI staining. The most circular nuclei are given a score of 1 (perfectly round nucleus). Nuclear area was measured in pixels and converted to μm$^2$ based on the spatial calibration table of ImageJ.

Statistical Analysis

Results are presented as means±standard deviation on the graphs for experiments done at least in triplicate. The data were analyzed using one-way analysis of variance (ANOVA) and Tukey's post-hoc test with P<0.05 considered significant.

EXAMPLES

Example 1

General Design of Microfluidic Device with Microchannels Combined with Paper Insert to Create a Chemical Gradient In this Example we show the general design of the microfluidic device with microchannels combined with paper insert to create a chemical gradient for the cell culture matrix.

Unless dealing with the respiratory tract, the mucosa or the skin, exposure to chemicals for most tissues in the body is mediated by the microenvironment. In the latter case, the chemical entities often diffuse toward cells over a short distance (from a blood vessel or upon production by cells or enzymes present in the surrounding matrix). Therefore, it seems important to provide cells with a continuous (or intermittent), yet controlled provision of the chemical of interest that diffuses through the ECM. Moreover, chemical exposure of cells might depend on the heterogeneity of the microenvironment. Cells might be present in different densities or within a matrix that possesses different characteristics (stiffness, presence of different cells types, etc.). Hence, depending on the microenvironment, the significant impact of a specific chemical might occur for different concentrations. Adopting a gradient feature to expose cells to a chemical of interest might shed light on the existence of thresholds for the cell response depending on the microenvironment.

Figure 10:
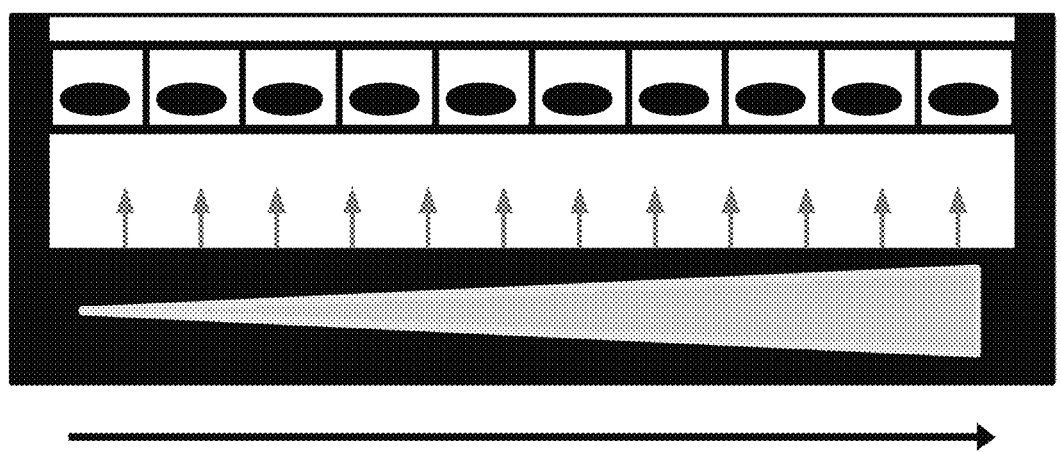
FIG. 10. Applying a chemical gradient in cell culture. A cell culture specimen model receives a chemical at increasing concentrations (as displayed by the widening triangle and the arrows) depending on the location in the culture area. Here cells of an epithelium are represented by rectangles with nuclei drawn in black, in the culture platform. With such system, it is possible to create controlled heterogeneity of the presence of the chemical throughout the culture surface. It is also possible to identify concentration thresholds for the impact of the chemical on cells depending on a given variation in cell culture parameters.

Cell culture has been traditionally performed with large quantities of medium added on top of the cells and changed every few days. Here we adopted a system with controlled fluid flow that would allow diffusion of the fluid into the cell culture area from underneath the cells. This system permits a relatively constant concentration of chemicals in a particular region of the cell culture with continuous replacement. It also helps avoiding the immediate dilution of the paracrine factors secreted by the cells into a large volume of medium. A simplified embodiment drawing of such gradient affected cell culture is shown in FIG. 10.

To create a gradient of the environmental chemical factor of interest, the microfluidic device was composed of a paper-based laminar bifurcating mixer unit placed underneath an open-access cell culture chamber (see materials and methods), hence enabling fluid diffusion upward. Perfusion of chemical species was obtained by placing the porous cell culture substrate made of cellulose acetate (with or without ECM coating) in the open chamber, directly on top the microfluidic open channels covered with a micro-aperture PET membrane, as shown on the explanatory drawings (FIG. 1A-D). Open culture chambers permit easy removal of the cell culture sample from the microfluidic platform for analysis.

To produce the gradient, the mixer was designed with two inlets for liquids containing different concentrations of the chemical of interest (a given concentration vs. zero). These liquids rapidly combine within multiple channels on a horizontal plane hence, creating a gradient from one pole of the rectangular cell culture window to the other. The channels empty into the cell culture chamber to create a fluid bed.

Figure 8:
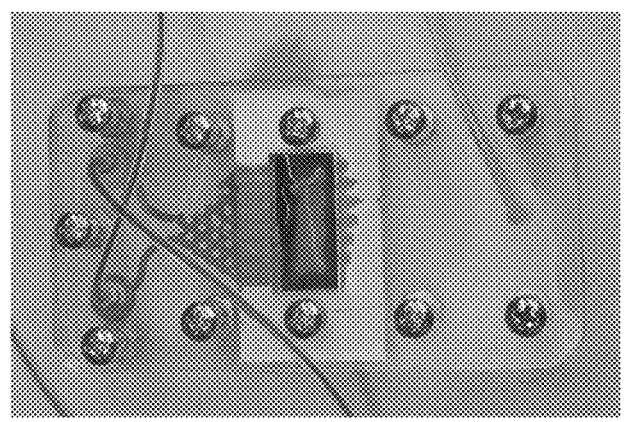

Unlike typical microfluidic networks that consist of hollow channels, the system presented here features a unique design via the incorporation of a paper insert within the channels. This type of assembly offers the advantages of wicking-assisted flow that improves flow uniformity among channels at low flow rates (compared to completely open channels), and provides a continuous gradient in the cell culture chamber. The same type of paper substrate serves as the cell culture substratum in the chamber, providing a uniform fluid bed; indeed, the intrinsic hydrophilicity of the paper inserts prevents the formation of liquid droplets or leaking in the chamber from the opened apertures (See FIG. 8). In fact, the capillary forces of the paper counteract the variations in liquid pressure induced by the interaction between the atmosphere and the fluidic network.

To assemble the five layers that make the device, the bottom acrylic base is covered by a PDMS substrate fabricated with microchannels on which a paper insert fills the channels, itself topped with a PET membrane punctured with micro-apertures. The final part is the top acrylic layer containing an insert (exposure aperture) to place the cell culture membrane (FIG. 1E-F).

Example 2

Validating ROS Gradient Production within a Homogeneous Cell Culture Fluid Bed

In this Example, we validated the microfluidic device with microchannels combined with paper insert and ROS gradient production within a homogeneous cell culture fluid bed.

Figures 2, 2A, 2B, 2C, 2D:
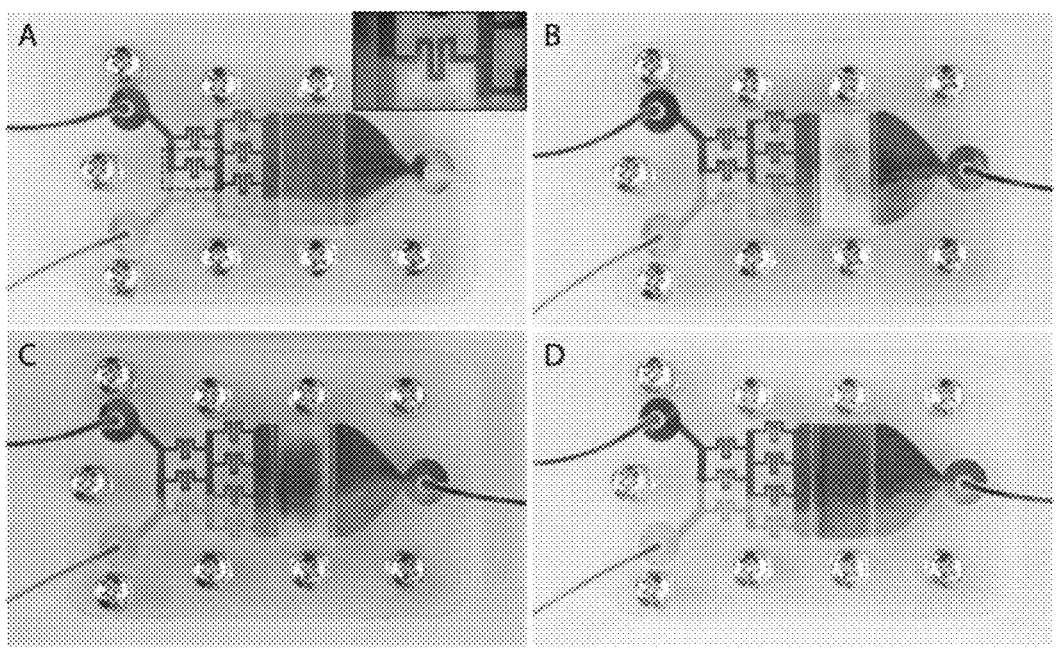
(FIG. 2A) Photograph of gradient formed in the device using red and blue dyes after one hour, without the cellulose acetate paper used for cell culture support in the cell culture chamber; inset shows a magnified image of the gradient mixer corresponding to the dash-line area.
(FIG. 2B-D) Time course of gradient formation in the presence of the cellulose acetate paper in the cell culture chamber: Image of gradient diffusion through the acetate cellulose paper after initial contact with the underlying microfluidic concentration gradient generator (FIG. 2B), after 8 minutes (FIG. 2C) and after 17 minutes (FIG. 2D), at which time the gradient is stable.

To visually test for gradient formation in the microchannels, red and blue dyes were injected into each inlet independently at 0.1 ml/h flow rate and allowed to mix within the gradient forming chamber (FIG. 2A), before distributing to the microchannels through which the gradient could diffuse onto the culture substrate (FIG. 2B-D). The performance of the open-access gradient generator was then validated using optical measurements, as well as a ROS-specific electrochemical approach.

Figures 3, 3A, 3B, 3C, 3D, 3E, 3F:
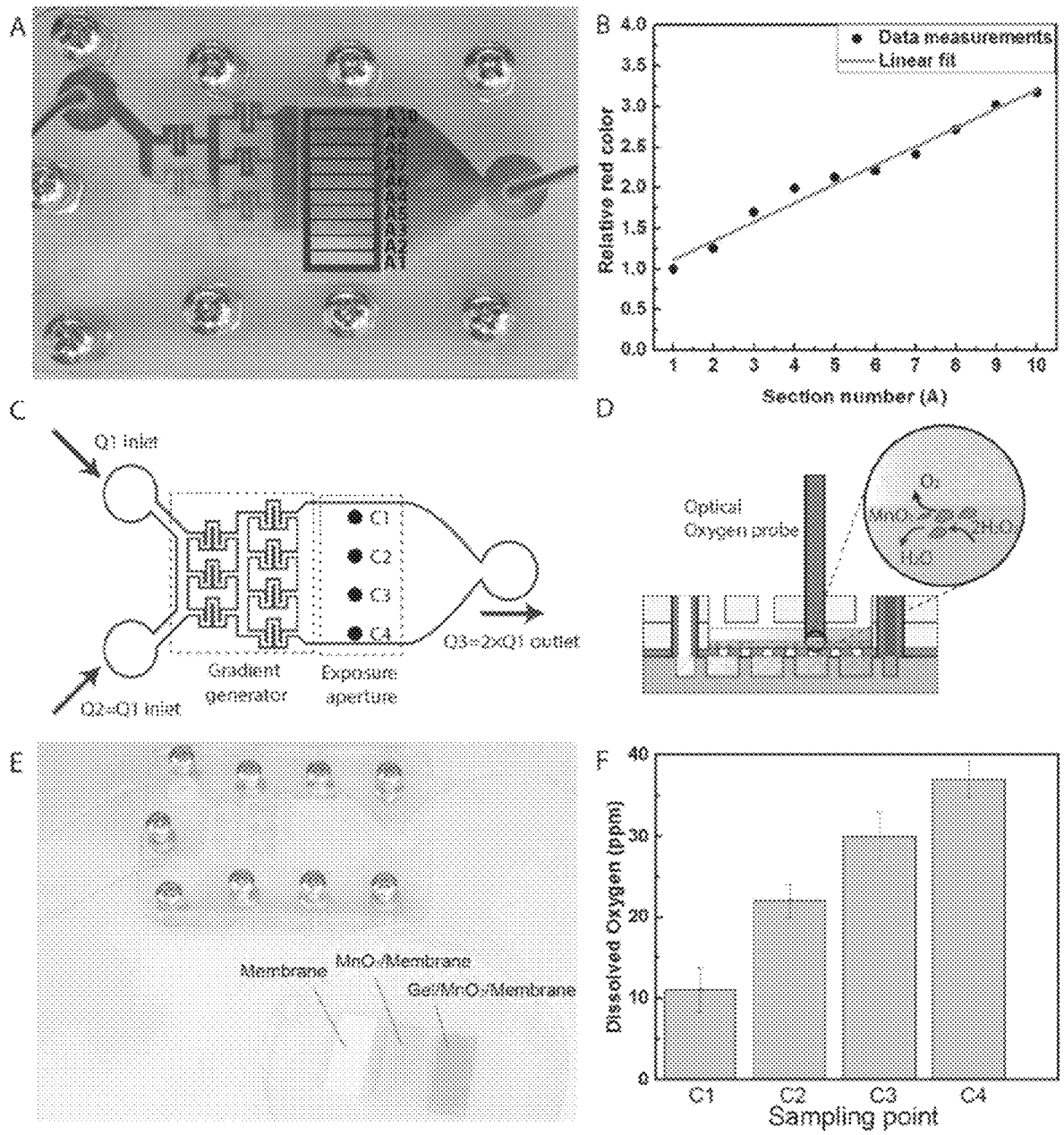
FIG. 3. A Gradient of reactive oxygen species (ROS) is generated in the open-access microfluidic device.
(FIG. 3A) Microfluidic concentration generator filled with red-dye and water solutions to create a color-based gradient. A rectangle with 10 even areas (A1 to A10) is drawn along the length of the cell culture chamber (also called exposure aperture).
(FIG. 3B) Representative graph showing color intensity at defined areas (A1 to A10) relative to A1 (the lowest measured) as a function of the distance along the chamber width.
(FIG. 3C) For the electrochemical measurement, ROS level was evaluated at four points (C1 to C4) along the exposure aperture while the inlets received 0.5% $H_2O_2$ and DI water. The outlet had twice the flow speed (Q3=2×Q1) of an inlet to compensate for the use of the two inlets necessary to produce the gradient.
(FIG. 3D) The ROS levels were indirectly measured upon catalytic conversion of $H_2O_2$ to oxygen by $MnO_2$ nanoparticles, using an optical oxygen probe. The schematic inside the circle illustrates the catalytic reaction.
(FIG. 3E) Photograph of the microfluidic device with the different parts used for the catalytic reaction: cellulose acetate membrane, addition of $MnO_2$ nanoparticles on the membrane ($MnO_2$/membrane), addition of agarose gel on top of the nanoparticles (Gel/$MnO_2$/membrane).
(FIG. 3F) Bar graph of dissolved oxygen levels at the selected sampling locations (C1 to C4) along the cell culture/exposure aperture. All locations have significantly different dissolved oxygen concentrations from each other.

Following injection of red-dyed water and undyed deionized water, respectively in each of the two inlets at the same flow rate, a gradient was visualized in the cell culture chamber (FIG. 3A). The open chamber was divided into 10 equal sections and the red color in each section was quantified relative to the section that had the lowest red color intensity. The concentration of red dye was indeed diluted by the gradient mixer and resulted in a linear increase in intensity from the low portion to the high portion of the gradient at a rate of 0.233 per 0.242 mm$^2$ (FIG. 3B).

Figures 9, 9A, 9B:
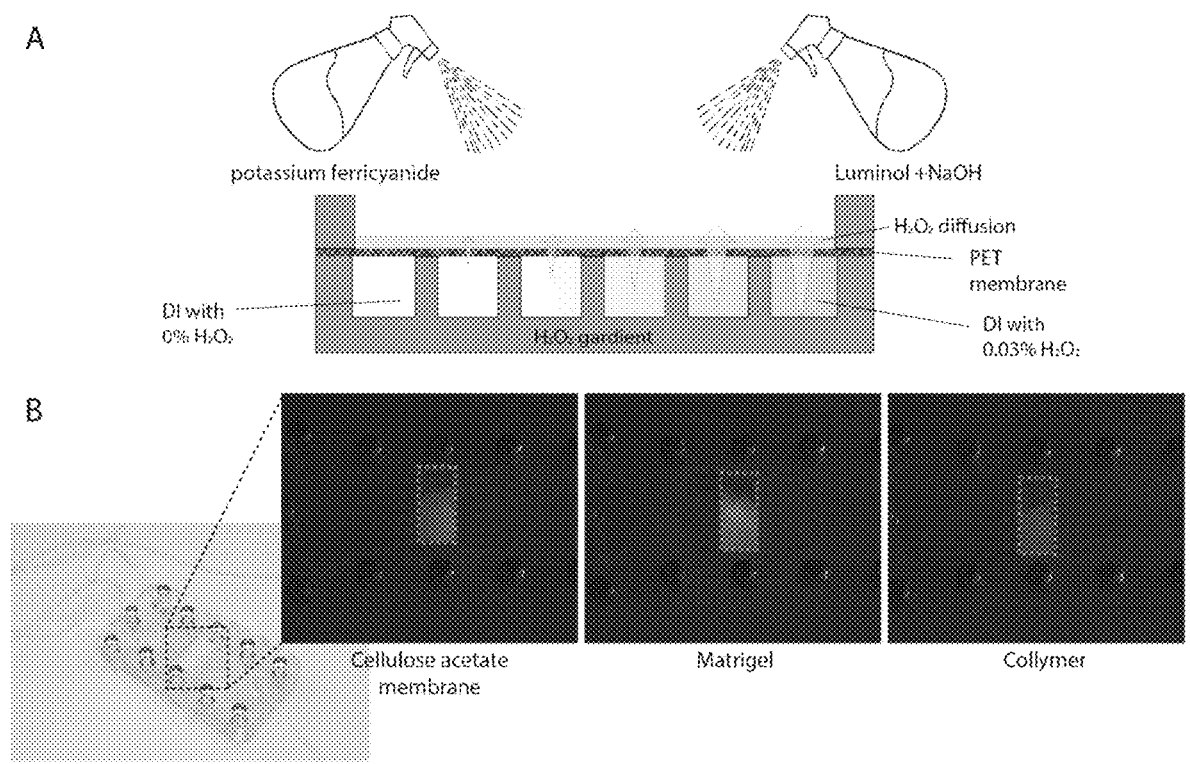
FIG. 9. Luminol-based assessment of the ROS gradient.
(FIG. 9A) Illustration of the technique used to visualize the ROS gradient in the microfluidic platform by spraying Luminol onto the bed fluid containing the ROS gradient.
(FIG. 9B) Blue color chemiluminescence gradient on different substrates, including pristine cellulose acetate substrate and cellulose acetate substrate covered with Matrigel or with Collymer. The dashed lines show the cell culture aperture in which the substrates were in contact with the gradient of $H_2O_2$.

In the electrochemical approach, a gradient of ROS was initiated by injecting 0.5% $H_2O_2$ in one of the inlets and deionized water in the other inlet. The ROS gradient was indirectly measured by converting $H_2O_2$ into oxygen via a catalyzing reaction, for which nanoparticles of $MnO_2$ were embedded in 2 mm agarose gel placed on the cellulose acetate cell culture membrane. Dissolved oxygen levels were measured at four locations along the gradient with a fiber-optic oxygen sensing probe, revealing concentration dilution towards the low portion of the gradient with recordings of 37, 30, 21, and 10 ppm (FIG. 3C-E). The cellulose acetate substrate covered with Matrigel or Collymers was permeable to liquid-containing ROS from the microchannels and reflected the existence of a gradient as shown by a luminol assay with changes in colors indicative of high and low ROS distributions (FIG. 9).

Example 3

Cellulose Acetate-Based Paper Substrate is Suitable for 2D and 3D Cell Cultures of Non-Neoplastic and Cancer Cells In this Example, we put paper substrate with the cell culture with or without extracellular matrix into the exposure aperture of the microfluidic device described in Example 1 and observed various cell's responses to the chemical gradient in the defined microenvironment.

Figures 4, 4A, 4B, 4C, 4D:
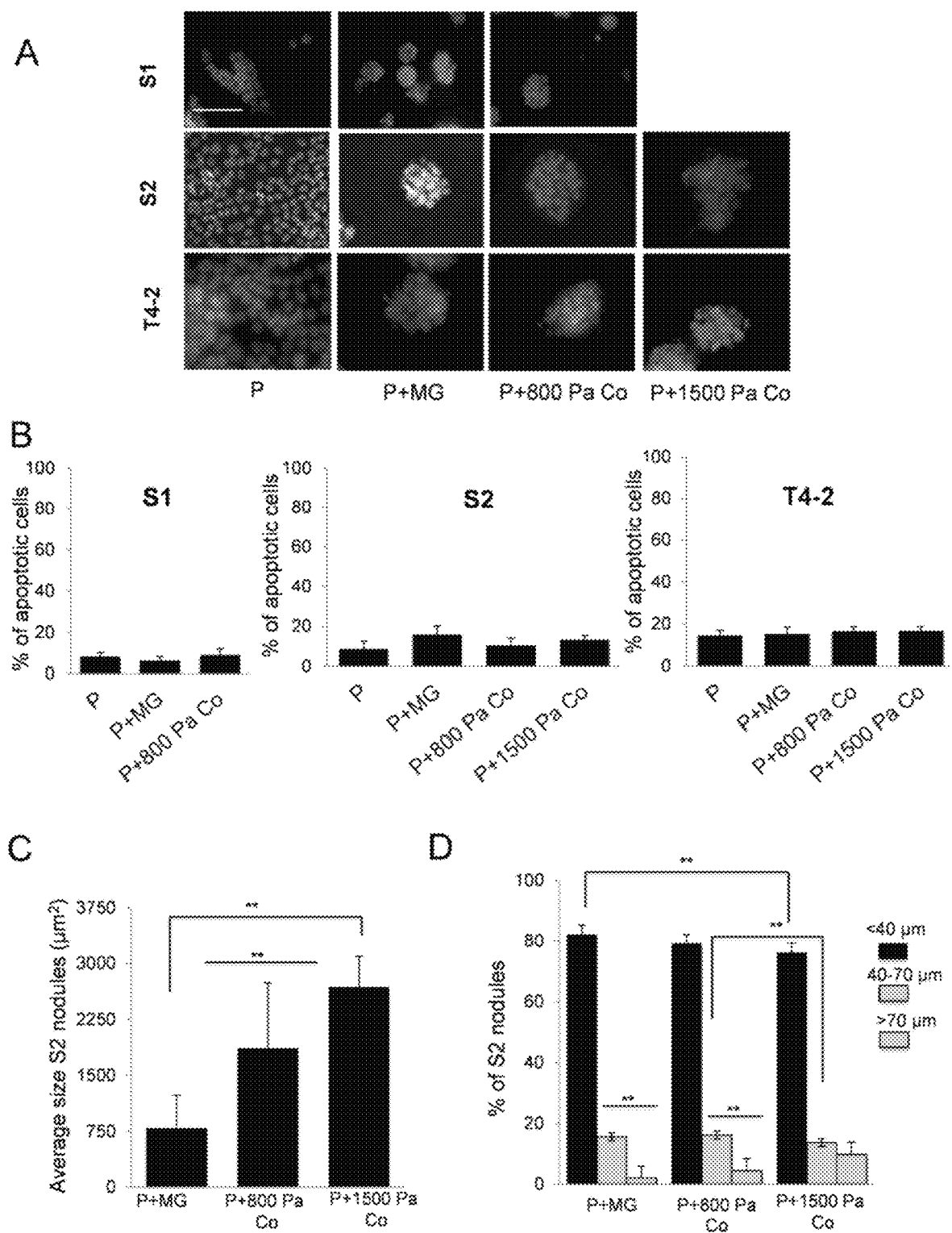
FIG. 4. Cellulose acetate paper substrate is amenable for both 2D and 3D cell culture. S1, S2 and T4-2 cells were cultured directly on cellulose acetate paper (P) for six days or in 3D culture, in the presence of Matrigel on cellulose acetate paper (P+MG) or Collymers at 800 Pa or 1500 Pa stiffness on cellulose acetate paper (P+800 Pa Co; P+1500 Pa Co) for eight days.
(FIG. 4A) Images of nuclei fluorescently stained with DAPI in cell monolayers produced in 2D culture (P) or spheroids (phenotypically normal acini and tumors) produced in 3D culture. Size bar, 50 µm.
(FIG. 4B) Bar graphs with percentages of cells with caspase-3 staining that reveal apoptosis under the different culture conditions; 150 cells were analyzed in three biological replicates.
(FIG. 4C) Bar graph of the average size of S2 tumor nodules under the different 3D cell culture conditions. Fifty nodules were assessed per group; n=3.
(FIG. 4D) Size based distribution (<40 µm; 40-70 µm; >70 µm) of S2 nodules under the different 3D cell culture conditions; fifty nodules were assessed per group; n=3. *$P<0.05$, $P<0.01$, *$P<0.001$ FIG. 5. The oxidative damage in S2 cells depends on ROS concentration range.

Three mammary epithelial cell types, non-neoplastic S1 cells, preinvasive or ductal carcinoma in situ (DCIS)-like S2 cells and invasive ductal carcinoma (IDC) T4-2 cells that belong to the HMT 3522 triple negative breast cancer progression series were tested for culture on the cellulose acetate-based paper substrate. These cell types correspond to tissues frequently exposed to microenvironmental ROS[24]. Cells were assessed for survival in standard 2D monolayer culture, and for survival and morphogenesis in 3D cell culture with two different types of extracellular matrix (ECM), Matrigel and Collymers, coated on the paper substrate. Matrigel is rich in basement membrane components such as collagen IV and laminin and corresponds to the direct ECM environment of non-neoplastic breast epithelium[21]. Collymers is a preparation based on collagen I and provides the possibility of modifying the stiffness degree of the matrix to better mimic cancer situations. Indeed, the normal stiffness (Young's modulus) of stromal matrix when measured in nonrestrained samples via indentation methods is around 800 Pa[25]; whereas stiffness increases in cancer with meaningful values to recreate cancerous conditions starting around 1500 Pa[26] Matrigel has been reported to correspond to normal matrix stiffness[27]. All cell types thrived on paper and showed usual rates of population survival (FIG. 4A-B). The non-neoplastic S1 cells formed small spheroids of the size of breast acini (~30 µm in diameter) in the presence of Matrigel and Collymers, and the neoplastic S2 and T4-2 cells formed tumor nodules in the presence of Matrigel and Collymers as well (FIG. 4A) when observed on day 8 of cell culture. Based on caspase 3 immunostaining there was approximately 5% cell death in 3D cell culture with Matrigel or Collymers (800 Pa and 1500 Pa) coated on paper in S1 and S2 populations; whereas T4-2 cells exhibited approximately 16% death (as routinely observed[28,29] in 3D cell culture regardless of the matrix conditions (FIG. 4B).

Interestingly, culture in Collymers increased the average nodule size in the S2 populations by ~2-fold (FIG. 4C). This cell line is characterized by heterogeneity in the sizes of nodules formed in culture with, upon day 8 of culture, a majority of nodules of small size (up to 40 µm), a lesser amount of nodules of intermediate size (40-70 µm) and few nodules above 70 µm.

It was shown previously that the larger the nodules, the more likely the progression towards an invasive phenotype[23]. When comparing the percentages of the different subpopulations of S2 nodules based on size, it appeared that S2 cells cultured within 800 Pa Collymers showed a higher percentage of intermediate size nodules than cells cultured within 1500 Pa Collymers (FIG. 4D). Knowing the suspected influence of ROS on triple negative breast cancer progression, it will be important to compare the effect of the gradient, not only depending on the type of matrix, but also depending on the nodule sizes.

Example 4

Cancer Cells Exhibit an Incremental Response Associated with Oxidative Stress when Exposed to the ROS Gradient, with an Impact Threshold for Nuclear Morphology Dependent on Matrix Stiffness In this Example, we have shown that the microfluidic device with ROS gradient to cancer cells make these cells exhibit increasing response associated with oxidative stress. In addition, the extracellular matrix stiffness also affects the nuclear morphology of cancer cells.

To determine the differential response to ROS depending on ECM characteristics and the extent of information that can be collected from using the gradient-on-a-chip, we focused on the preinvasive S2 cells. These cells respond to ROS (FIG. 5A) and correspond to triple negative DCIS, a breast cancer subtype for which progression to invasive behavior is thought to be influenced by oxidative stress[9].

One of the well-known consequences of exposure to ROS is the induction of oxidative DNA damage measured by 8-hydroxy-deoxyguanosine (8-OHdG)[30], and standard DNA damaged consisting of double strand breaks measured by γ-H2AX[31]. Cultures of S2 tumor nodules on day 8 were exposed to a gradient of ROS generated by injecting 250 µM $H_2O_2$ in culture medium in one of the inlets and only cell culture medium in the other inlet for four hours. Evidence of ROS-induced injury was assessed by western blot analysis of 8-OHdG and the percentage of cells with γ-H2AX staining. The tests were performed by splitting the cell cultures into three parts, corresponding to low, medium and high ROS concentrations. The split was achieved by cutting the membrane into equal pieces along the length of the exposure chamber for western blot analysis, or by performing immunofluorescence staining on intact cell culture membranes and randomly taking images of cells or tumor nodules within each of three equal areas of the cell culture membrane along the length of the exposure chamber.

The S2 cells in the low ROS concentration tier did no show oxidative DNA damage based on 8-OHdG expression, whereas there was a significant, but similar increase of 8-OHdG levels with medium and high ROS concentration tiers in both 2D cell culture and 3D Matrigel cell culture (FIG. 5B), confirming cellular injury induced by a certain level of ROS in the gradient-on-a-chip.

Figures 5, 5A, 5B, 5C:
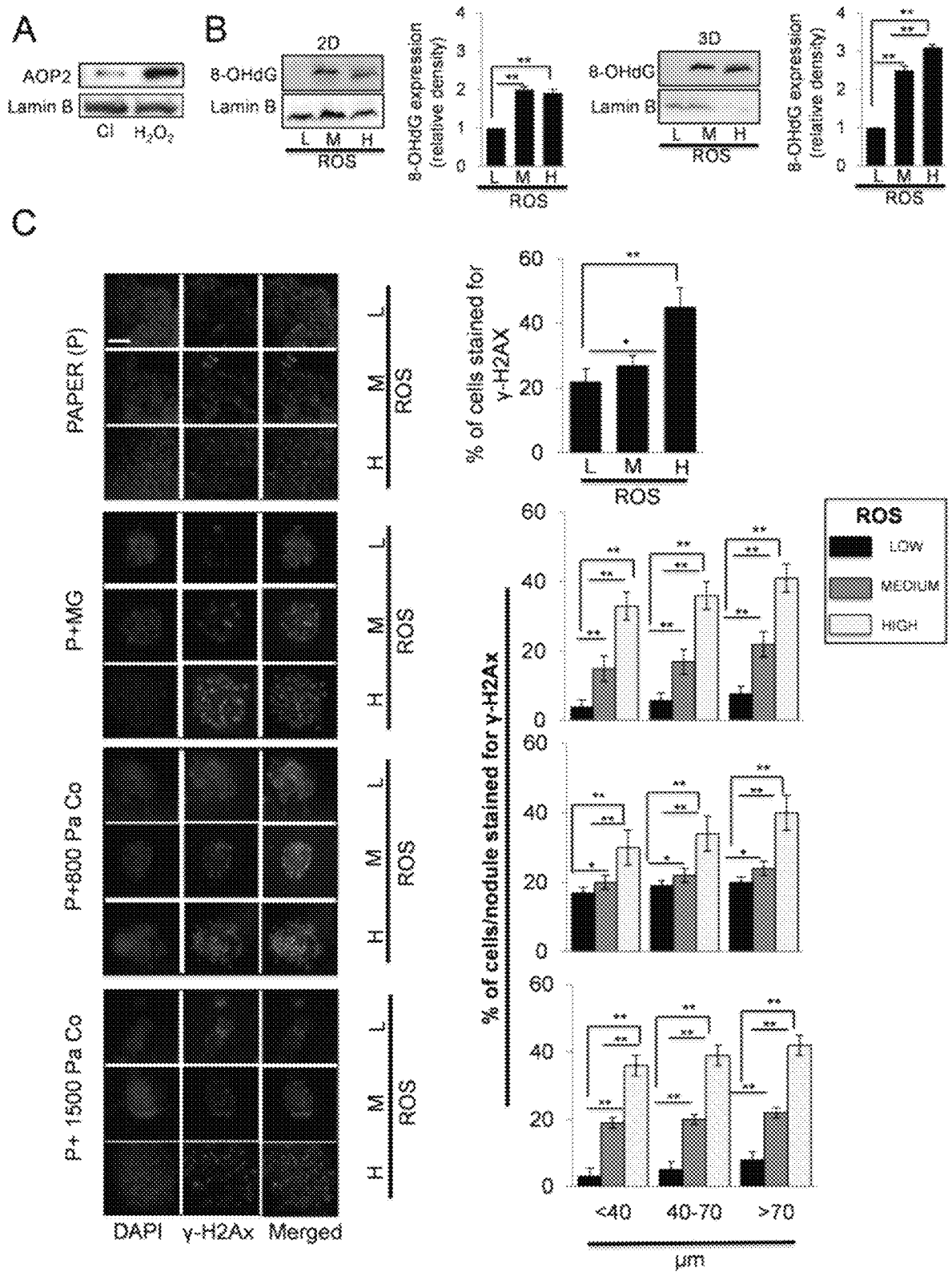
(FIG. 5A) Western blot image of AOP2 expression in S2 cells in 3D Matrigel culture treated with $H_2O_2$ (250 µm) for four hours compared to control (C1). Lamin B is used as loading control.
(FIG. 5B) Western blot for 8-OHdG expression in S2 cells cultured on paper alone (2D) and paper+Matrigel (3D) as a response to low (L), medium (M) and high (H) concentration tiers of $H_2O_2$. Lamin B is used as loading control. Adjacent bar graphs are densitometric quantifications of 8-OHdG expression normalized to Lamin B.
(FIG. 5C) Immunostaining for γ-H2AX (red staining) in S2 cells in 2D culture on cellulose acetate paper (P) and 3D culture, including paper+matrigel (P+MG), Paper+Collymers at 800 Pa stiffness (P+800 Pa Co) and Paper+Collymers at 1500 Pa stiffness (P+1500 Pa Co), under low (L), medium (M) and high (H) ROS concentration tiers [each concentration tier corresponds to the analysis of ⅓ of the total paper area along the increasing gradient in the exposure chamber]. Nuclei are stained with DAPI (blue). Size bar, 50 µm. Bar graphs adjacent to images for each culture condition represent the percentages of cells positive for γ-H2AX staining in 2D culture or per tumor nodule depending on nodule size (<40 µm, 40-70 µm, and >70 µm) in 3D culture. A total of 150 nuclei were analyzed in 2D and all nuclei were analyzed in an average of 50 images of nodules per size group in 3D culture; n=3. *$P<0.05$, $P<0.01$, *$P<0.001$ FIG. 6. S2 cells protective response to oxidative stress occurs in a gradient-dependent manner, with the exception of the high matrix stiffness condition. S2 cells were kept in 2D culture on acetate cellulose paper (P) for six days or in 3D culture for eight days [paper+matrigel (P+MG), Paper+Collymers at 800 Pa stiffness (P+800 Pa Co) and Paper+Collymers at 1500 Pa stiffness (P+1500 Pa Co)] before being exposed to the $H_2O_2$ gradient for four hours. Left panel: Immunofluorescence staining for AOP2 (red) and counterstaining of nucleus with DAPI (blue) of cells in low (L), medium (M), and high (H) $H_2O_2$ concentration tiers [each concentration tier corresponds to the analysis of ⅓ of the total paper area along the increasing gradient in the exposure chamber]. Size bar, 50 µm. Right panel: Bar graphs adjacent to each culture condition show the percentage of cells (2D culture) or nodules (3D culture) that express AOP2 under different concentration tiers of $H_2O_2$. A total of 150 nuclei were analyzed in 2D culture and an average of 50 nodules were assessed per 3D culture condition; n=3. *$P<0.05$, $P<0.01$, *$P<0.001$ FIG. 7. The impact of ROS gradient on cell nucleus morphology depends on the stiffness of the ECM. The S2 cells were cultured on 2D (P) for six days, or in 3D culture including paper+matrigel (P+MG), Paper+Collymers at 800 Pa stiffness (P+800 Pa Co) and Paper+Collymers at 1500 Pa stiffness (P+1500 Pa Co) before being exposed to the $H_2O_2$ gradient for four hours.

Analysis of γ-H2AX by immunostaining enabled us to obtain an appreciation of the cellular impact of ROS depending on the size range of the tumor nodules. Regardless of the culture conditions, there was a significant increase in the percentage of cells stained with γ-H2AX when comparing low, intermediate and high concentration tiers (FIG. 5C). However, the low ROS concentration tier started at less than 5% of cells with γ-H2Ax staining in Matrigel culture and 1500 Pa Collymers culture compared to 20% for cells cultured on paper or under 800 Pa Collymers. As expected, sensitivity was highest regardless of the concentration tiers for S2 cells cultured under 2D conditions. Interestingly, all culture conditions led to a similar response level (around 40%) of the cell population in the high concentration tier; however, when comparing nodules of low, intermediate and large sizes (<40 µl m; 40-70 µl m; >70 µl m) it appeared that higher damage level had a tendency to correlate with higher nodule size. From these results it seems that both basement components-rich ECM and high level stiffness collagen I might protect the preinvasive cells against low levels of ROS.

Figure 6:
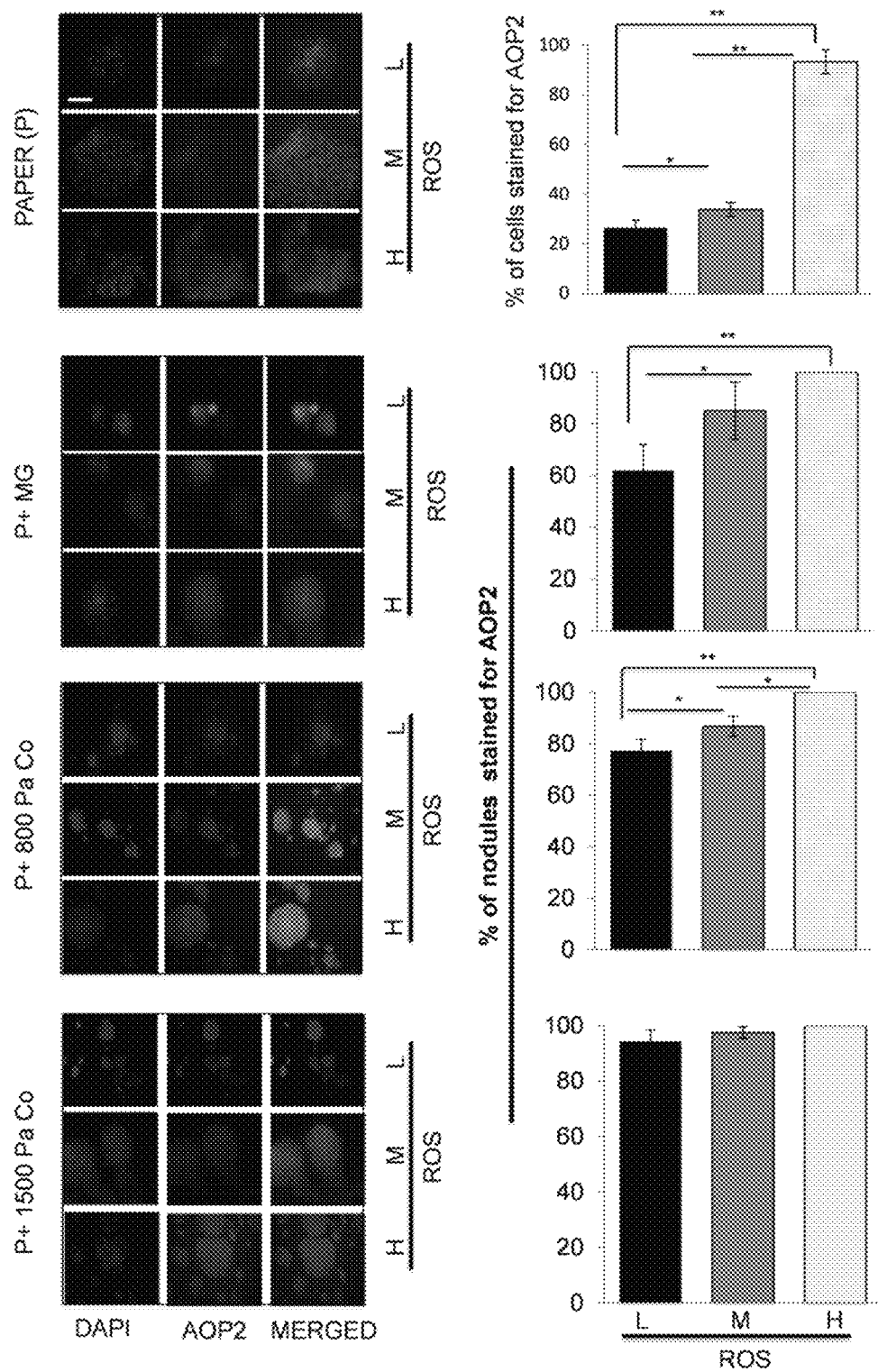
Figures 7, 7A, 7B, 7C, 7D:
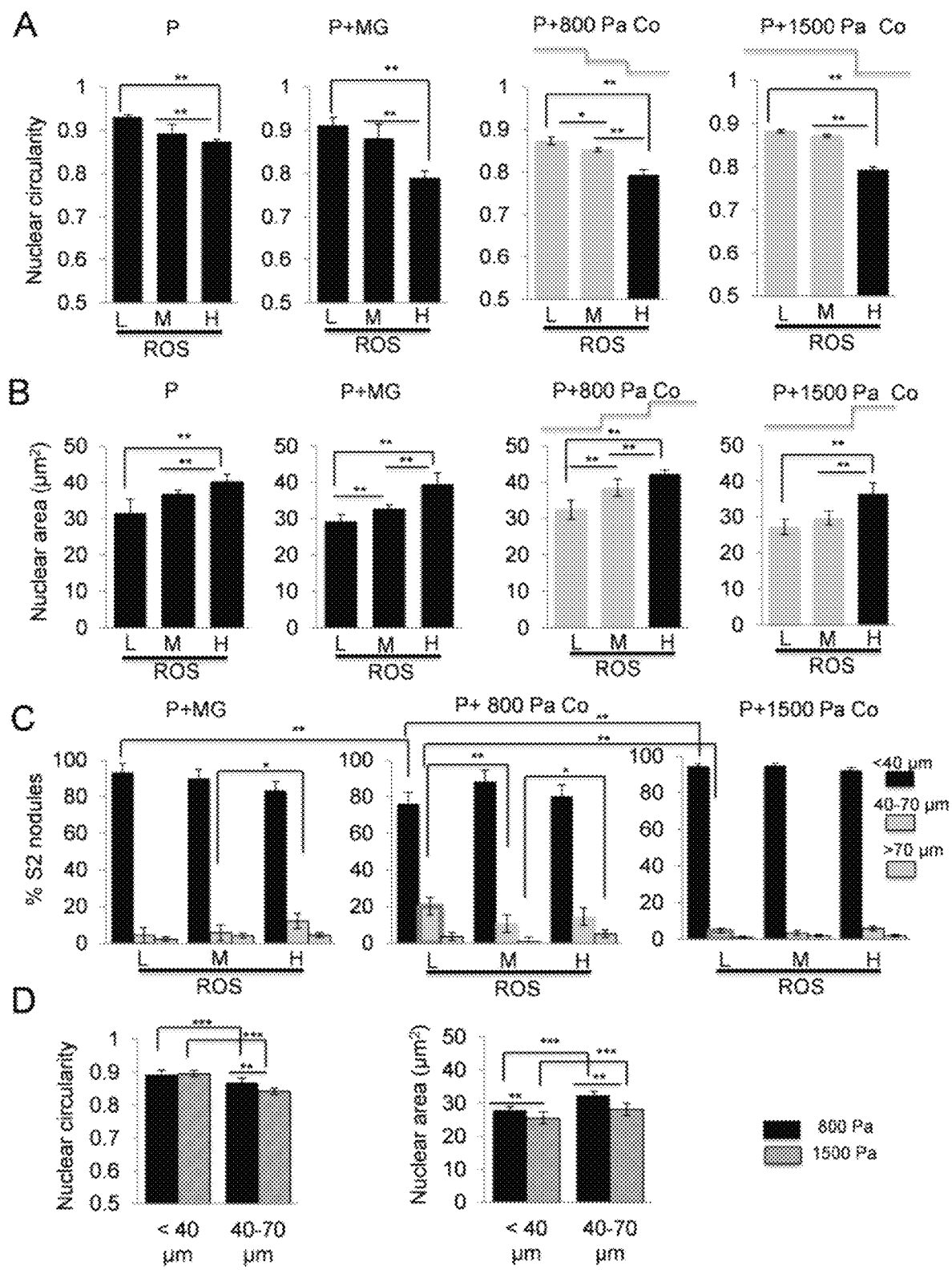
(FIG. 7A) Average nuclear circularity measured using Image J (the most circular nuclei are given a score of 1) depending on low (L), medium (M) and high (H) ROS concentration tiers under the different culture conditions [each concentration tier corresponds to the analysis of ⅓ of the total paper area along the increasing gradient in the exposure chamber].
(FIG. 7B) Average nuclear area measured using Image J. A total of 150 nuclei were analyzed in 2D culture and an average of 100 nuclei was assessed per group in 3D culture for area and circularity; n=3. Bars in gray represent behavior differences between 800 Pa and 1500 Pa Collymers cultures; the 'stepwise' gray line drawing above the graphs indicates for which passages between tiers of ROS concentration the nuclear morphology significantly changes in each culture condition [straight line=no change; step-like lines=significant change].
(FIG. 7C) Bar graph of the percentages of S2 nodules in the different size categories (<40 µm, 40–70 µm, and >70 m) under low (L), medium (M) and high (H) ROS concentration tiers. The thick gray lines around bars for intermediate size nodules in P+800 Pa Co and P+1500 Pa Co highlight the significant difference in the percentages of nodules in this size category between the two culture conditions.
(FIG. 7D) Comparison of nuclear circularity and nuclear area between and within S2 nodule size categories cultured in 800 Pa Collymers and 1500 Pa Collymers and exposed to low ROS concentration tier. *$P<0.05$, $P<0.01$, *$P<0.001$ FIG. 8. Leakage without paper insert. Red and blue dyes introduced into inlets mix within the microfluidic platform, but the fluid leaks out of the open aperture if the paper insert is not present.

The response to ROS exposure in early stages of cancer might be accompanied with protective mechanisms against ROS, notably via the increased production of anti-oxidant protein 2 (AOP2)[32] Upon staining AOP2 is localized in the cytoplasm, and thus, it does not permit single cell analysis in tumor nodules. Instead for 3D culture, we performed the analysis on a per nodule basis, determining the percentage of nodules stained or not for AOP2 in a given ROS concentration tier. Like for markers of DNA damage, there was a significant dose-dependent increase in AOP2 expression with increasing ROS concentrations in the presence of Matrigel and 800 Pa Collymers, although Matrigel culture was not associated with further significant increase between medium and high ROS concentration tiers (FIG. 6). Surprisingly, S2 nodules revealed almost 100% AOP2 response regardless of the ROS levels. Therefore, like for DNA damage induction, the protective oxidative stress response induced by ROS appears dependent on the matrix characteristics, with a significant impact of increased matrix stiffness. An important observation is the increase in nuclear area and decrease in nuclear circularity that accompany induction of oxidative stress. These changes in the morphology of the cell nucleus are unlikely to be consequences of the sole DNA damage, since DNA damage is not listed among the important factors in the control of nuclear size and shape[14]. Instead, modifications in nuclear morphology are proposed to be linked with changes in cell phenotype, as it is known that invasive tumor cells often have increased nuclear size compared to the normal cells or their preinvasive counterpart In support of the rationale that nuclear morphological changes are associated with changes in cell phenotype is the fact that modifications in nuclear morphology have been associated with altered chromatin arrangement, thus, possibly affecting gene expression and cancer progression[14]. Staining with DAPI was used to measure nuclear area and circularity. All culture conditions were accompanied with changes in nuclear morphology upon exposure to ROS gradient, confirming the impact of oxidative stress on the cell nucleus. Nuclear circularity decreased with increasing ROS concentration tiers, with the lowest circularity achieved in 3D cultures compared to 2D culture. Interestingly, like for DNA damage measured via γH2AX, the behavior of cells in the presence of Matrigel was similar to that of cells cultured in 1500 Pa collymers, with a significant decrease in nuclear circularity only between medium and high ROS concentration tiers (FIG. 7A). Nuclear area was increased by ROS exposure regardless of the cell culture condition, with significance obtained between the same ROS concentration tiers as for circularity depending on the cell culture condition, with the exception of Matrigel between low and medium tiers (FIG. 7B). Like for nucleus circularity, the behavior of cells in 1500 Pa compared to 800 Pa Collymers was different, with a significant modification already when going from low to medium ROS concentration tiers for the cells in 800 Pa Collymers. Moreover, the increase in nuclear area was the highest in 800 Pa Collymers culture for all ROS concentration tiers when compared to Matrigel and 1500 Pa Collymer cultures. Therefore, like for the impact of ROS on DNA, the response to oxidative stress in cells measured based on nuclear morphology, although with similar trends, displays subtle differences depending on ECM characteristics. Since both nuclear circularity and nuclear area responded differently depending on the ROS concentration tiers when comparing cell cultures in Collymers of different stiffness, we also assessed the impact of the culture condition on the percentage of nodules in the different size categories. Indeed, the percentage of small nodules was lower and the percentage of nodules with intermediate size was higher in 800 Pa Collymers compared to 1500 Pa Collymers (FIG. 7C).

To assess whether the difference in nuclear morphology response was dependent on the nodule size, the data on nuclear circularity and area in the low ROS tier were reanalyzed taking into account the nodule size category. Results show that, regardless of the Collymers stiffness, the area of the cell nucleus positively correlates with the nodule size, and nuclear circularity negatively correlates with the nodule size, which indicates that nodules of increasing sizes have a nuclear morphology characteristic of generally more aggressive tumors. However, while increased matrix stiffness leads to decreased nuclear area regardless of the nodule size, it has a stronger influence on cells included in larger tumors nodules compared to smaller nodules to decrease nuclear circularity (FIG. 7D). We conclude that the higher percentage of intermediate size nodules in 800 Pa Collymers compared to 1500 Pa Collymers might be the reason for the higher sensitivity of the cells to ROS, with alterations in nuclear area and circularity potentially indicative of initial phenotypic changes toward cancer progression under this culture condition.

Importantly, our results demonstrate that the levels of injury and oxidative stress response in the three different tiers of ROS concentration depend on characteristics of the ECM. Normally induction of oxidative stress in the fibroblasts of the stroma is accompanied with increased matrix stiffness[9]. To reproduce this phenomenon and only study the impact of matrix stiffness on cancer cells, we used a tunable collagen I matrix. The ROS gradient revealed that depending on the matrix stiffness, the cancer cells responded differently to the same increment in ROS concentration. This was the case for well-known parameters associated with oxidative stress (γH2AX and AOP2), as well as with morphological parameters of the cell nucleus, such as area and circularity.

The impact on the nuclear morphological parameters is particularly important to assess in light of the potential link with changes in gene expression and phenotype. The increase in area and decrease in circularity were in agreement with previous observations for cells under oxidative stress[33], and these changes might be in-line with nuclear morphological changes that accompany cancer progression[40]. It appeared that a higher stiffness might require higher levels of ROS to induce nuclear morphological changes compared to lower stiffness levels, suggesting that the cellular responses to ROS might depend on the microenvironment. This differential response to ROS might occur even within a same cancerous tissue if the microenvironment is heterogeneous, which could account for the tumor heterogeneity that is being increasingly reported[41].

The comparison of the behavior of the different parameters studied might lead to some interesting directions to pursue. For instance, the impact of ROS gradient on nuclear circularity was the lowest in 2D culture compared to 3D culture and the impact on γH2AX expression was the highest, raising the possibility that these nuclear features respond to ROS in an independent manner. Comparing γH2AX and AOP2 responses in tumors in 1500 Pa Collymers also suggested that the protective AOP2 response might be independent from the level of DNA damage induction.

It was also puzzling to observe that cells cultured in Matrigel and 1500 Pa Collymers responded similarly to the ROS gradient for γH2AX and nuclear circularity although they have a different matrix stiffness and composition. To better grasp the underlying mechanisms governing such differences, it seems that taking into account cancer heterogeneity (illustrated in this study via the differences in tumor nodule sizes) and thus, the heterogeneity of nuclear morphology before chemical exposure might be worthwhile.

Preventing sustained exposure to ROS via increased cellular detoxification had been shown early on to induce phenotypic changes characterized by decreased aggressiveness in breast cancer cells[42]. We have demonstrated with the gradient-on-a-chip that the level of ROS exposure significantly affects the extent of the cellular response, notably for nuclear morphology that is considered as a potential marker of phenotypic changes[43]. Another important parameter to consider is exposure time; here, exposure was short (four hours), but nuclear morphological changes were already observed. The gradient-on-a-chip can be used over several days of ROS exposure in future studies to determine whether changes in nuclear morphology are indeed accompanied with the acquisition of an invasive behavior of tumor nodules. The gradient-on-a-chip platform is also amenable for coculture of tumors with fibroblasts and other cell types of interest in order to progressively acquire a more comprehensive picture of the microenvironmental impact on the response to ROS exposure.

Example 5

Risk-On-a-Chip for Breast Cancer

Figure 11:
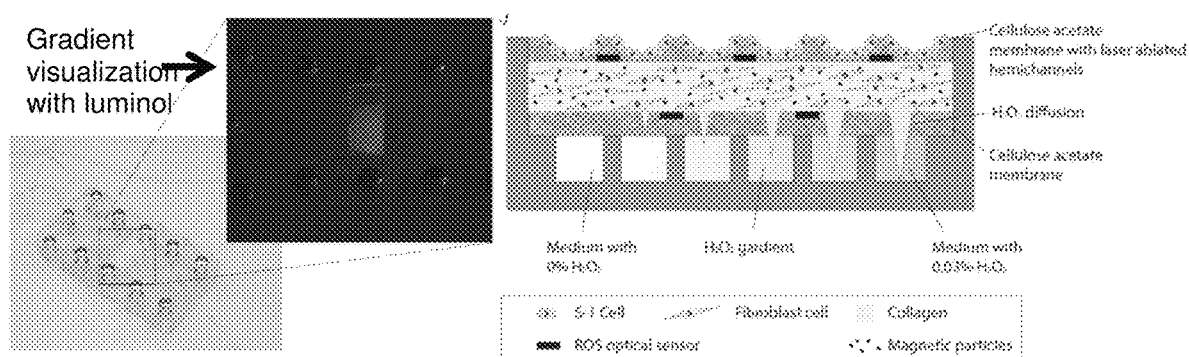
FIG. 11. Risk-on-a-chip: image of gradient on-a-chip with drawing to the right of a co-culture system inside the culture chamber. The stroma is topped by hemichannels lined by epithelial cells (these two layers represent stacked and separable cultures each on a cellular acetate support allowing individual analysis of each tissue type). The mechanical stability of the cellulose acetate membrane facilitates stacking and de-stacking of the layers for biochemical extractions or microscopy imaging of each tissue type. Reactive oxygen species ($H_2O_2$) are brought as a gradient to test their impact on normal tissue homeostasis. Biosensors can be attached to the cellulose acetate supports or mixed with the stroma.

In this example, we create a culture chamber that contains a stacked co-culture of tissues. See FIG. 11, wherein an image of gradient on-a-chip with drawing to the right is shown that a co-culture system lays inside the culture chamber. The stroma is topped by hemichannels lined by epithelial cells (these two layers represent stacked and separable cultures, each on a cellular acetate support allowing individual analysis of each tissue type). A full disclosure of hemichannels is found in the U.S. patent application Ser. No. 14/577,326. The content of which is incorporated herein entirely.

Figure 12:
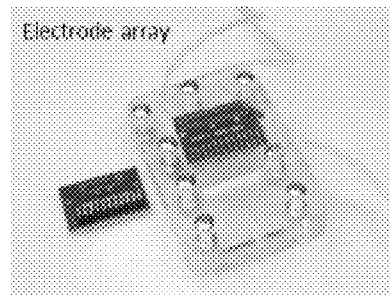
FIG. 12. The gradient on-a-chip equipped with a system of electrodes (green platform). The electrode array may be on top of the chamber (or coming from the bottom) to measure oxygen or oxidizing molecules or a mixture of these molecules in real time.

The mechanical stability of the cellulose acetate membrane facilitates stacking and de-stacking of the layers for biochemical extractions or microscopy imaging of each tissue type. Reactive oxygen species ($H_2O_2$) are brought as a gradient to test their impact on normal tissue homeostasis. Additional biosensors shown in FIG. 12, for example, an electrode array can be attached to the cellulose acetate supports or mixed with the stroma.

Example 6

Figures 13, 13A, 13B, 13C:
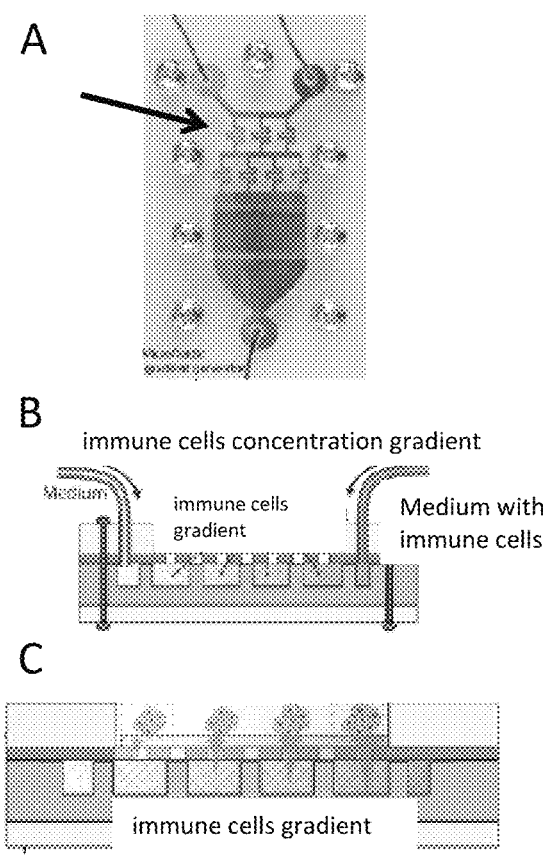
FIG. 13. Gradient-on-a-chip device with a gradient of cells mimicking the flow of immune cells from the blood into the stroma.
FIG. 13A. Red and blue dyes show the mixing in the gradient generator area (arrow). Wires indicate the two fluid inlets (top) and single fluid outlet (bottom).
FIG. 13B. Cross-sectional view from the side with fluidic inlets (arrows), with constant flow rate to create a stable concentration gradient within the cell culture aperture. The increasing gradient is shown as darkening pink color.
FIG. 13C. Representation of the tumors in the cell culture chamber with purple arrows indicating the increasing arrival of cells (e.g., immune cells such as natural killer [NK] cells) from the gradient.

A Gradient of Cells (to Mimic the Extravasation of Immune Cells) with or without a Gradient of Chemicals In this example, we create Gradient-on-a-chip device with a gradient of cells mimicking the flow of immune cells from the blood into the stroma. See FIG. 13, wherein panel A shows red and blue dyes, indicating mixing in the gradient generator area (arrow). Wires indicate the two fluid inlets (top) and single fluid outlet (bottom). Panel B is a cross-sectional view from the side with fluidic inlets (arrows), with constant flow rate to create a stable concentration gradient of cells with or without chemicals within the cell culture aperture. The increasing gradient is shown as darkening pink color. Panel C is representation of the tumors in the cell culture chamber with purple arrows indicating the increasing arrival of cells (e.g., immune cells such as natural killer [NK] cells) from the gradient.

The invention claimed is:

1. An open cell culture device for creating a "gradient on a chip", comprising from bottom to top:
    an optically transparent and machinable bottom fixture;
    a moldable/castable silicone/rubber material-based microfluidic spacer with laser defined microchannels;
    a paper bifurcating mixer, wherein the dimensions of the paper bifurcating mixer are configured to fit into the microchannels of the microfluidic spacer;
    an optically transparent polymer film-based membrane with laser defined micro-apertures, wherein the micro-apertures are positioned downstream to the microchannels; and
    an optically transparent and machinable cover fixture with an exposure aperture as cell culture chamber, and at least two inlets and one outlet for tubing,
    wherein said optically transparent and machinable cover fixture and said optically transparent polymer film-based membrane have aligned holes that connect to said paper bifurcating mixer and said microfluidic spacer configured to allow said at least two inlets and one outlet to pass through and directly reach the microfluidic microchannels,
    wherein said at least two inlets and one outlet are configured to go through said aligned holes, from top to bottom, in the optically transparent and machinable cover fixture and the optically transparent polymer film-based membrane, and reach the paper bifurcating mixer that is inserted in the microfluidic spacer, wherein said two inlets are on the side of bifurcating channels for mixing two fluids and said one outlet is on the opposite side of the bifurcating channels to collect fluids from the microchannels.

2. The open cell culture device of claim 1, further comprising a smooth hydrophilic cellulose-based film for cell culture over the area of micro-apertures of the polymer film-based membrane, wherein said area of micro-apertures allows fluid to go up from the laser-defined microchannels of the microfluidic spacer into the exposure chamber where cells are cultured.

3. The open cell culture device of claim 1, wherein the microchannels are about 200 μm deep.

4. The open cell culture device of claim 1, wherein the micro-apertures are evenly distributed over an area of the exposure aperture's size, configured to have adequate access to an underlying chemical gradient and to maintain the stiffness to keep the paper mixer inside the microchannels.

5. The open cell culture device of claim 1, wherein the bottom and cover fixtures are acrylic plate with each about 5 mm thick.

6. The open cell culture device of claim 1 wherein the paper bifurcating mixer is porous hygroscopic material that is cellulose-based providing capillary forces for continuous, leak-less flow.

7. The open cell culture device of claim 1, wherein the paper-based mixer is a hydrophilic cellulose-based film.

8. The open cell culture device of claim 1, wherein the moldable/castable silicone/rubber material-based microfluidic spacer is made of polydimethylsiloxane (PDMS).

9. The open cell culture device of claim 1, wherein the optically transparent polymer-based membrane is polyethylene terephthalate (PET) membrane.

* * * * *